United States Patent [19]

McKinnon

[11] Patent Number: 5,792,055
[45] Date of Patent: Aug. 11, 1998

[54] GUIDEWIRE ANTENNA

[75] Inventor: Graeme C. McKinnon, Zurich, Switzerland

[73] Assignee: Schneider (USA) Inc., Plymouth, Minn.

[21] Appl. No.: 752,431

[22] Filed: Nov. 19, 1996

Related U.S. Application Data

[63] Continuation of Ser. No. 311,700, Sep. 23, 1994, abandoned.

[30] Foreign Application Priority Data

Mar. 18, 1994 [EP] European Pat. Off. ............ 94104329

[51] Int. Cl.$^6$ ................................................ A61B 5/055
[52] U.S. Cl. ............................................ 600/410; 600/424
[58] Field of Search ............................ 128/653.2, 653.5, 128/653.1, 899, 657; 600/407, 410, 421, 434, 424; 324/318, 322, 307, 309

[56] References Cited

U.S. PATENT DOCUMENTS

| | | | |
|---|---|---|---|
| 4,865,047 | 9/1989 | Chou et al. | 607/101 |
| 4,960,106 | 10/1990 | Kubokawa et al. | 128/653.5 |
| 5,170,789 | 12/1992 | Narayan et al. | 128/653.5 |
| 5,211,166 | 5/1993 | Sepponen | 128/653.5 |
| 5,271,400 | 12/1993 | Dumoulin et al. | 128/653.2 |
| 5,347,221 | 9/1994 | Rubinson | 128/653.5 |
| 5,348,010 | 9/1994 | Schnall et al. | 128/653.2 |
| 5,358,515 | 10/1994 | Hurter et al. | 607/101 |
| 5,427,103 | 6/1995 | Fujio et al. | 128/653.5 |

FOREIGN PATENT DOCUMENTS

| | | |
|---|---|---|
| 0091577A1 | 10/1983 | European Pat. Off. . |
| 0165742B1 | 12/1985 | European Pat. Off. . |
| 0300147A1 | 1/1989 | European Pat. Off. . |
| 0385367A1 | 9/1990 | European Pat. Off. . |
| 3937052A1 | 5/1990 | Germany . |
| 8704080 | 7/1987 | WIPO . |

OTHER PUBLICATIONS

Camart et al, Coaxial Antenna Array for 915 MHZ Interstitial Hyperthermia: Design and Modelization–Power Deposition and Heating Pattern—Phase Array, IEEE Transactions on Microwave Theory and Techniques 40 December, No. 12 (1992).

*Primary Examiner*—Brian L. Casler
*Attorney, Agent, or Firm*—Faegre & Benson LLP

[57] ABSTRACT

A medical appliance for use in magnetic resonance imaging procedures. A guidewire for vascular procedures is formed by a coaxial cable acting as antenna in a magnetic resonance imaging system.

27 Claims, 1 Drawing Sheet

GUIDEWIRE ANTENNA

CONTINUING DATA

This application is a continuation of application Ser. No. 08/311.700, filed 23 Sep., 1994, now abandoned.

BACKGROUND OF THE INVENTION

This invention relates to a medical appliance for use in magnetic resonance imaging procedures performed on a body, comprising an antenna detecting magnetic resonance response signals, the antenna intended to be inserted into the body for interacting with a magnetic resonance procedure for calculating the position of the medical appliance in the body.

Tracking of catheters and other devices positioned within a body may be achieved by means of a magnetic resonance imaging system in order to avoid using X-rays and the risk of accumulated X-ray dose to the patient and long term exposure to the attending medical staff.

Typically, such a magnetic resonance imaging system may be comprised of magnet means, pulsed magnetic field gradient generating means, a transmitter for electromagnetic waves in radio-frequency, a radio-frequency receiver, a processor, and a controller. The device to be tracked has attached to its end a small coil of electrically conductive wire. The patient is placed into the magnet means and the device is inserted into the patient. The magnetic resonance imaging system generates electromagnetic waves in radio-frequency and magnetic field gradient pulses that are transmitted into the patient and that induce a resonant response signal from selected nuclear spins within the patient. This response signal induces current in the coil of electrically conductive wire attached to the device. The coil thus detects the nuclear spins in the vicinity of the coil. The radio-frequency receiver receives this detected response signal and processes it and then stores it with the controller. This is repeated in three orthogonal directions. The gradients cause the frequency of the detected signal to be directly proportional to the position of the radio-frequency coil along each applied gradient.

The position of the radio-frequency coil inside the patient may therefore be calculated by processing the data using Fourier transformations so that a positional picture of the coil is achieved. Since however the coil only reacts, literally not a positional picture of the coil but in fact a positional picture of the position of the response signals inside the patient is achieved. Since this positional picture contains no information yet on the region surrounding the immediate vicinity of the coil, this positional picture can be superposed with a magnetic resonance image of the region of interest. In this case the picture of the region may have been taken and stored at the same occasion as the positional picture or at any earlier occasion.

Radio-frequency antennas in the form of a coil couple inductively to the electromagnetic field and they allow obtaining a substantially spatially uniform magnetic field which results in a relatively uniform image intensity over a wide region. The problem is however that coil configurations are bulky (the received signal is determined by the loop diameter) and cannot be implemented for use in narrow vessels, whereby their use for the placement of medical appliances such as catheters may be critical.

Furthermore, the spot image which is provided for by the coil antenna does not allow knowing or even evaluating the orientation of the device; as a result, the magnetic resonance imaging system cannot be used for steering the device into tortuous areas such as blood vessels.

European Patent No 0165742 describes a catheter for use with magnetic resonance imaging systems. This catheter comprises a sheath which has embedded within the wall thereof a pair of conductors preferably formed of a foil composite obtained by plating of conductive materials of selected magnetic susceptibility to yield a composite of desired susceptibility substantially matching that of the sheath. In this way, the magnetic invisibility of the catheter is maintained. The tip of the catheter contains a loop connecting the conductors, the plane of such a loop being preferably transverse to the catheter symmetry axis. As explained in the document, when excited by a weak pulse source, the loop supports a dipole magnetic field which locally distorts the magnetic resonance image providing an image cursor on the magnetic resonance imaging display, and a low magnetic susceptibility functional element such as a light pipe threaded into the catheter sheath allows direction of the catheter through selected blood vessels. The essence of this structure is thus the accurate location and monitoring of the catheter tip.

However, this is achieved within the environment of a bulky configuration which cannot be advanced through narrow vessels and which cannot be steered by reference to the magnetic resonance imaging system.

The document WO 87/04080 shows surgical catheters composed of alternating annular segments of non-magnetic materials which are highly opaque to nuclear magnetic resonance examination and less opaque, respectively. These catheters have thin coatings of silicone rubber on their external surface as well as on the internal surface of their main central lumen. A plurality of further lumens are distributed circumferentially within the catheter wall and guidance wires are housed in said lumens, secured at the distal end of the catheter wall and coupled to a joystick at the proximal end of the catheter for individual tightening and relaxing to permit radial guidance of the distal end of the catheter. The central lumen of the catheter and still further secondary lumens arranged in the catheter wall are for the distribution of various drugs or for surgical tools such as optic fiber for laser surgery or suturing devices or still stitching grippers. By these arrangements, location of the catheters is apparent under nuclear magnetic resonance examination, visually at the distal end. These structures are however bulky and they have the same drawbacks as outlined hereinbefore.

European Patent Application published under N 0385367 shows an insertable prostate pick-up probe devised for being a nuclear magnetic resonance receiving device capable of imaging spectra from the human prostate and surrounding tissue; this probe may also be used as the transmit coil for radio-frequency excitation. This probe is intended to be used with an interface network providing the tuning, impedance matching, and decoupling functions, and including a connection to a magnetic resonance imaging scanner.

The probe includes a shaft supporting a patient interface balloon at its distal end, comprising an inner balloon and an outer balloon, the inner balloon being capable of being inflated with air supplied through a lumen within the shaft. A non-stretchable lane formed of an adhesive backed cloth material partly covers the inner balloon and serves as a guide for a flexible receiving coil arranged between the inner balloon and the outer balloon, this coil being electrically connected to the interface via an insulated cable extending through the shaft. Upon inflation, the non-stretchable plane rises and forces the receiving coil and outer balloon against the region of interest so that the receiving coil is in position to receive the best possible radio-frequency signal from the region of interest. Special indentations forming a shell are provided on the outer balloon to act as coil positioners when the balloon is in its uninflated state so that the coil may be repeatedly positioned relative to the shell inside the outer balloon for numerous clinical inflation and deflation cycles. A colored stripe is marked on the shaft, possibly including a scale, for indicating the distance which the shaft has been inserted into the patient and also the radial orientation of the balloon for proper alignment with the region of interest. In operation, the probe is inserted while the patient interface balloon is in the uninflated state; the alignment stripe marked on the shaft is used to radially and longitudinally position the probe within the region of interest. Once the probe is correctly placed, the patient interface balloon is inflated and the receiving coil is forced against the region of interest. The probe is then connected to the interface network via the insulated cable.

This particular arrangement of the radio-frequency coil does not reduce the bulk of the system which cannot be used for narrow or tortuous vessels. Furthermore, the system does not provide for any information as to orientation of the probe for steering purposes.

The document DE-3937052 A1 shows a biopsy tube for use in a magnetic resonance imaging procedure, comprising longitudinally extending coaxial conductor tubes separated by insulator tubes and extending the length of the biopsy tube. In a further embodiment, the conductor tubes are replaced by gutter like portions of coaxial conductor tubes which are separated by an insulator filling. Here again, the result is a bulky configuration which cannot be advanced to narrow vessels. In addition, that kind of assembly is substantially stiff, thereby further preventing the applicability of the instrument in tortuous vessels.

SUMMARY OF THE INVENTION

The object of this invention is to improve the possibilities of using magnetic resonance imaging procedures by means of a medical appliance which is simple and efficient, which may continuously provide a full information as to its position and orientation, which occupies a minimal space and which has a great flexibility so as to be capable of reaching narrow and tortuous vascular configurations, which may be actually steered under magnetic resonance imaging, which may be used as an interventional means, and which may also prove efficient in the determination of the vascular configurations.

To this effect, the medical appliance according to the invention complies with the definitions given in the claims.

As opposed to the coil configuration, the open wire length antenna couples capacitively to the electromagnetic field and as the received signal originates from the immediate neighborhood of the open wire length, it becomes possible to obtain an image of the antenna, of its position, as well as of its orientation. Steering of the appliance is thus actually possible. The open wire length antenna may be extremely thin and it may also have a high flexibility, allowing safe driving and passage through vascular configurations, even in tortuous and restricted areas thereof. This opens way to using magnetic resonance imaging procedures in interventional conditions where time and precision are of the essence. By repeatedly measuring, reconstructing, and displaying the image with a very short image repetition time, a magnetic resonance imaging fluoroscopy system can be created. And one could also use the open wire length antenna to make a high resolution image of a vessel wall.

According to a simple inexpensive embodiment, the open wire length antenna may be formed by a coaxial cable.

According to an embodiment aiming very thin configurations, the open wire length antenna may be made of a coaxial cable in which the shield and insulators are respectively made of a conductor coating and insulating coatings. In both these cases, the first and second conducting elements of the coaxial configuration may have the same length or unlike lengths.

According to a further embodiment, also aiming very thin configurations, the open wire length antenna may be made of two conducting strands insulated from one another, twisted or parallel to one another. And these strands may have the same length or unlike lengths.

The open wire length antenna may be included in a catheter and the like. As opposed to coil antennas for which the received signal depends on the loop diameter, the diameter of the open wire length antenna is of secondary relevance and, therefore, the open wire length antenna may be devised to form the whole or part of a guidewire as used in vascular procedures for the positioning of catheters and the like.

DESCRIPTION OF THE DRAWINGS

These and other objects will become readily apparent from the following detailed description with reference to the accompanying drawings which show, diagrammatically and by way of example only, four embodiments of the invention.

DETAILED DESCRIPTION

Figure 1:
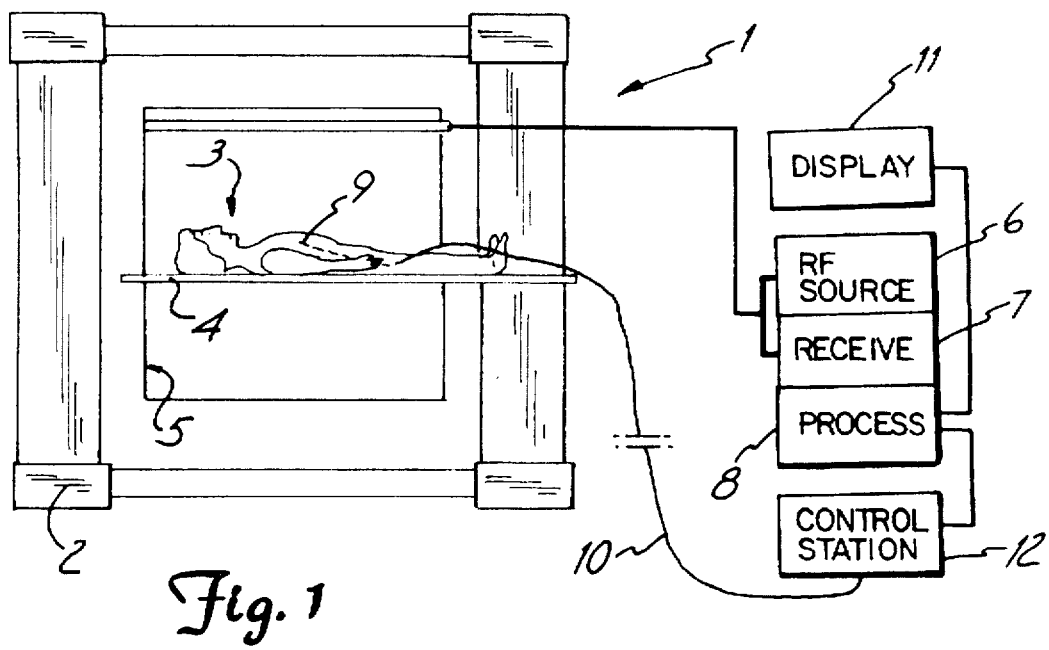
FIG. 1 is a block diagram of a system environmental to the present invention.

The system shown in FIG. 1 is a magnetic resonance imaging apparatus 1 comprising a magnet system 2 for generating a homogeneous magnetic field on a subject 3 placed on a support table 4. Inside the magnet system 2 is a coil structure 5 to produce around the subject a magnetic field obtained from radio-frequency energy source 6. Receiver 7 responds to the resonance signal and processor 8 reconstitutes the integers of the projection which will be shown on display 11. The medical appliance 9, inserted into subject 3, is connected via conductor 10 to control station 12. Such a general configuration is familiar to those skilled in the art and it will not be described in further detail.

Figure 2:
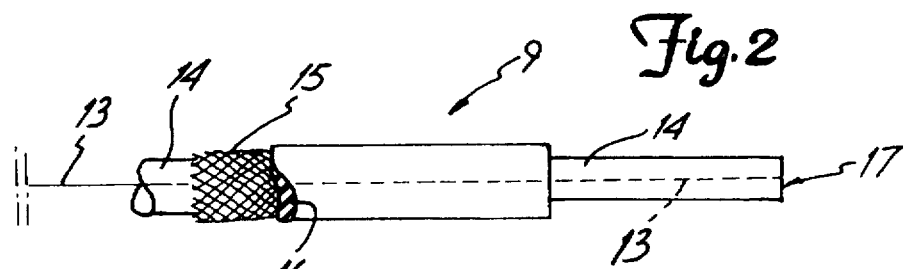
FIG. 2 is a longitudinal part section of a first embodiment of the appliance according to the invention.

The appliance 9, as exemplified in FIG. 2, is a guidewire including an open wire length antenna formed by a coaxial cable comprising a central conductor 13 enclosed in an insulator 14 surrounded by a shield 15 encased in an insulator 16. As used in this application, an open wire length includes an open-ended or un-delimited piece of wire, as opposed to a closed wire length such as a piece of wire with a coil configuration at the end. The shield 15 and the outer insulator 16 of the coaxial cable have been removed from a portion distal end 17. The proximal end (not shown) of the coaxial cable is for connection to the standard antenna input of control station 12 as generally shown in FIG. 1.

Figure 3:
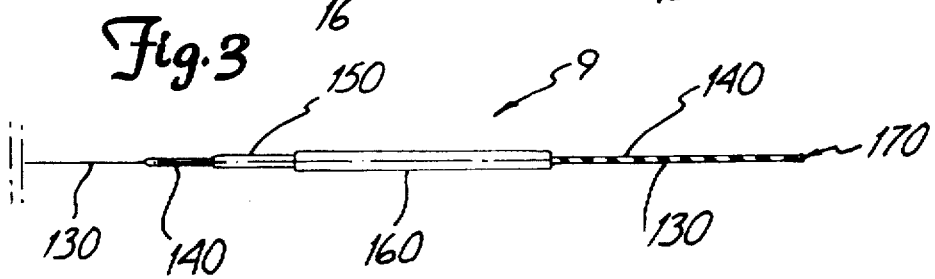
FIG. 3 is a longitudinal part section of a second embodiment of the appliance according to the invention.

The appliance 9 of FIG. 3 is also a guidewire including an open wire length antenna formed by a coaxial cable.

However, the insulator 140 surrounding the central conductor 130 is replaced by an insulating coating 140, while the shield 15 is replaced by a conductor coating 150 and the insulator 16 by an insulator coating 160. As for the embodiment of FIG. 3, the conductor coating 150 and insulator coating 160 have been removed from a portion of the distal end of tip 170. Also, the proximal end (not shown) of this coaxial cable is adapted to connection to the standard antenna input of control station 12 (FIG. 1).

Variants may be envisaged.

For instance, the outer conductor and insulator, 15–16 resp. 150–160, need not be removed from a portion of the distal end 17 resp. 170. Similarly, the outer conductor and insulator may be removed a far greater length from the distal end 17 resp. 170, and it is also possible to have them removed to the proximal end of the guidewire, outside of the patient.

Subject to the precautions or requirements inherent to patient protection, it would be also possible to have the guidewire comprised of a naked conductor 13 or 130, while the insulator 14 or 140 and outer conductor 15, 150 and insulator 16, 160 would be installed towards the proximal end of the guidewire, outside of the patient.

Similarly, the coaxial configuration shown is not compulsory, being possible to have the open wire length antenna as a naked or insulated wire with appropriate polarities arranged for connection thereof to the antenna input of the control station.

Figure 4:
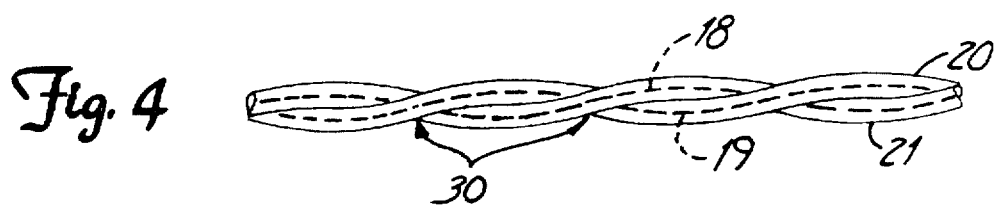
FIGS. 4 and 5 are longitudinal views of two further embodiments of the appliance according to the invention.

FIG. 4 shows one such possibility, in which the open wire length antenna is made of two twisted conducting strands 18 and 19 insulated from one another by appropriate coatings 20 and 21.

Figure 5:
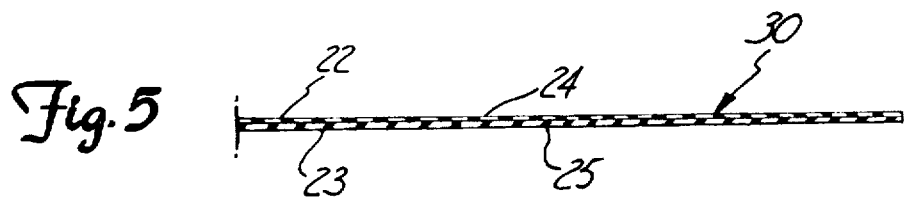

FIG. 5 also shows one such possibility, in which the open wire length antenna is made of two conducting strands 22 and 23 parallel to one another and separated by insulator coatings 24 and 25.

As for the previous embodiments, the strands 18 and 19, respectively 22 and 23, may have the same length or unlike lengths.

In both the embodiments of FIG. 4 and FIG. 5, the channels 30 which are left open along the insulated strands may be used for further investigation purposes when the open wire length antenna is placed in the lumen of a catheter, for example for pressure readings.

I claim:

1. A medical appliance comprising an elongated signal-receiving antenna for detecting and providing magnetic resonance response signals, the antenna adapted to be inserted into the body during magnetic resonance imaging procedures and for providing the response signals used for calculating a position of the medical appliance in the body, wherein the antenna comprises an open wire length including first and second conductor means having proximal ends adapted and arranged for interconnection to a receiver to couple the detected resonance response signals to the receiver, spaced-apart distal ends, and at least a first insulator means for physically separating and electrically insulating adjacent portions of the first and second conductor means, the distal ends of the first and second conductor means and the at least first insulator means adapted and arranged for exposure to a field of electromagnetic energy during a magnetic resonance procedure to couple electromagnetic energy from the field into the antenna and detect and provide the magnetic resonance response signals to the proximal ends of the conductor means.

2. A medical appliance according to claim 1, wherein the open wire length antenna is formed of a coaxial cable including the first and second conductors in a coaxial arrangement.

3. A medical appliance according to claim 1, wherein the open wire length antenna is formed of a cable having the first conductor enclosed in the first insulator, the first insulator surrounded by the second conductor and the second conductor encased in a second insulator, and wherein said first conductor and second conductor have the same length.

4. A medical appliance according to claim 1, wherein the open wire length antenna is formed of a cable having the first conductor enclosed in the first insulator, the first insulator surrounded by the second conductor, and the second conductor encased in a second insulator, and wherein said first conductor and second conductor have unlike lengths.

5. A medical appliance according to claim 1, wherein the open wire length antenna is made of the first conductor, the first insulator includes a first insulating coating applied on said first conductor, the second conductor includes a conducting coating surrounding said first insulating coating, and the antenna further includes a second insulating coating applied on said conducting coating, and wherein said first conductor and conducting coating have the same length.

6. A medical appliance according to claim 1, wherein the open wire length antenna is made of the first conductor, the first insulator includes a first insulating coating applied on said first conductor, the second conductor includes a conducting coating surrounding said first insulating coating, and the antenna further includes a second insulating coating applied on said conducting coating, and wherein said first conductor and conducting coating have unlike lengths.

7. A medical appliance according to claim 1, wherein the first and second conductors of the open wire length antenna include conducting strands insulated from one another.

8. A medical appliance according to claim 7, wherein the first and second conductor means are parallel to one another.

9. A medical appliance according to claim 7, wherein the first and second conductor means are twisted.

10. A medical appliance according to claim 7, wherein the first and second conductor means have the same length.

11. A medical appliance according to claim 7, wherein the first and second conductor means have unlike lengths.

12. A medical appliance according to claim 1, wherein the open wire length antenna forms at least a part of a guidewire for vascular procedures.

13. A medical appliance antenna system for use in connection with magnetic resonance imaging procedures, including:

a medical appliance comprising an elongated signal-receiving antenna for detecting and providing magnetic resonance response signals, the antenna adapted to be inserted into the body during magnetic resonance imaging procedures and for providing the response signals used for calculating a position of the medical appliance in the body, wherein the antenna includes an open wire length including first and second conductors having proximal ends adapted and arranged for interconnection to a receiver to couple the detected response signals to the receiver, spaced-apart distal ends, and at least a first insulator for physically separating and electrically insulating adjacent portions of the first and second conductors, the distal ends of the first and second conductors and the at least first insulator adapted and arranged for exposure to a field of electromagnetic energy during a magnetic resonance procedure to couple the electromagnetic energy from the field to the antenna and detect and provide the magnetic resonance response signals to the proximal ends of the conductors; and a receiver electrically connected to the antenna for receiving the magnetic resonance response signals and providing information representative of the position of the medical appliance.

14. A medical appliance according to claim 13, wherein the open wire length antenna is formed of a coaxial cable including the first and second conductors in a coaxial arrangement.

15. A medical appliance according to claim 13, wherein the open wire length antenna is formed of a cable having the first conductor enclosed in the first insulator, the first insulator surrounded by the second conductor and the second conductor encased in a second insulator, and wherein said first conductor and second conductor have the same length.

16. A medical appliance according to claim 13, wherein the open wire length antenna is formed of a cable having the first conductor enclosed in the first insulator, the first insulator surrounded by the second conductor, and the second conductor encased in a second insulator, and wherein said first conductor and second conductor have unlike lengths.

17. A medical appliance according to claim 13, wherein the open wire length antenna is made of the first conductor, the first insulator includes a first insulating coating applied on said first conductor, the second conductor includes a conducting coating surrounding said first insulating coating, and the antenna further includes a second insulating coating applied on said conducting coating, and wherein said first conductor and conducting coating have the same length.

18. A medical appliance according to claim 13, wherein the open wire length antenna is made of the first conductor, the first insulator includes a first insulating coating applied on said first conductor, the second conductor includes a conducting coating surrounding said first insulating coating, and the antenna further includes a second insulating coating applied on said conducting coating, and wherein said first conductor and conducting coating have unlike lengths.

19. A medical appliance according to claim 13, wherein the first and second conductors of the open wire length antenna include conducting strands insulated from one another.

20. A medical appliance comprising an elongated and signal-receiving antenna for detecting and providing magnetic resonance response signals, the antenna adapted to be inserted into the body during magnetic resonance imaging procedures and for providing the response signals used for calculating a position of the medical appliance in the body, wherein the antenna comprises an open wire length including first and second conductors having proximal ends adapted and arranged for interconnection to a receiver to couple the detected resonance response signals to the receiver, spaced-apart distal ends, and at least a first insulator for physically separating and electrically insulating adjacent portions of the first and second conductors, the distal ends of the first and second conductors and the at least first insulator adapted and arranged for exposure to a field of electromagnetic energy during a magnetic resonance procedure to couple electromagnetic energy from the field into the antenna and detect and provide the magnetic resonance response signals to the distal ends of the conductors.

21. A medical appliance according to claim 20, wherein the open wire length antenna is formed of a coaxial cable including the first and second conductors in a coaxial arrangement.

22. A medical appliance according to claim 20, wherein the open wire length antenna is formed of a cable having the first conductor enclosed in the first insulator, the first insulator surrounded by the second conductor and the second conductor encased in a second insulator, and wherein said first conductor and second conductor have the same length.

23. A medical appliance according to claim 20, wherein the open wire length antenna is formed of a cable having the first conductor enclosed in the first insulator, the first insulator surrounded by the second conductor, and the second conductor encased in a second insulator, and wherein said first conductor and second conductor have unlike lengths.

24. A medical appliance according to claim 20, wherein the open wire length antenna is made of the first conductor, the first insulator includes a first insulating coating applied on said first conductor, the second conductor includes a conducting coating surrounding said first insulating coating, and the antenna further includes a second insulating coating applied on said conducting coating, and wherein said first conductor and conducting coating have the same length.

25. A medical appliance according to claim 20, wherein the open wire length antenna is made of the first conductor, the first insulator includes a first insulating coating applied on said first conductor, the second conductor includes a conducting coating surrounding said first insulating coating, and the antenna further includes a second insulating coating applied on said conducting coating, and wherein said first conductor and conducting coating have unlike lengths.

26. A medical appliance according to claim 20, wherein the first and second conductors of the open wire length antenna include conducting strands insulated from one another.

27. A medical appliance according to claim 20 and further including a receiver electrically connected to the antenna for receiving the magnetic resonance response signals and providing information representative of the position and orientation of the medical appliance.

* * * * *